US009914726B2

(12) United States Patent
Hoekstra et al.

(10) Patent No.: US 9,914,726 B2
(45) Date of Patent: Mar. 13, 2018

(54) 2-(2,4-DIFLUOROPHENYL)-1,1-DIFLUORO-1-(5-SUBSTITUTED-PYRIDIN-2-YL)-3-(1H-TETRAZOL-1-YL)PROPAN-2-OLS AND PROCESSES FOR THEIR PREPARATION

(71) Applicant: Viamet Pharmaceuticals, Inc., Durham, NC (US)

(72) Inventors: William J. Hoekstra, Durham, NC (US); Daniel Knueppel, Zionsville, IN (US); Jim Renga, Indianapolis, IN (US); Gregory Whiteker, Carmel, IN (US); Michael T. Sullenberger, Westfield, IN (US)

(73) Assignee: VPS-3, INC., Durham, NC (US)

( * ) Notice: Subject to any disclaimer, the term of this patent is extended or adjusted under 35 U.S.C. 154(b) by 0 days.

(21) Appl. No.: 15/126,345

(22) PCT Filed: Mar. 19, 2015

(86) PCT No.: PCT/US2015/021519
§ 371 (c)(1),
(2) Date: Sep. 15, 2016

(87) PCT Pub. No.: WO2015/143188
PCT Pub. Date: Sep. 24, 2015

(65) Prior Publication Data
US 2017/0081316 A1  Mar. 23, 2017

Related U.S. Application Data

(60) Provisional application No. 61/955,661, filed on Mar. 19, 2014.

(51) Int. Cl.
C07D 401/06 (2006.01)
C07D 413/06 (2006.01)
C07D 213/127 (2006.01)
A01N 43/713 (2006.01)

(52) U.S. Cl.
CPC ......... *C07D 413/06* (2013.01); *A01N 43/713* (2013.01); *C07D 213/127* (2013.01); *C07D 401/06* (2013.01)

(58) Field of Classification Search
CPC .................................................. C07D 401/06
USPC ...................................................... 546/268.4
See application file for complete search history.

(56) References Cited

U.S. PATENT DOCUMENTS

| 4,426,531 | A | 1/1984 | Bison et al. |
| 8,236,962 | B2 | 8/2012 | Hoekstra et al. |
| 8,748,461 | B2 | 6/2014 | Hoekstra et al. |
| 8,754,227 | B2 | 6/2014 | Hoekstra et al. |
| 8,796,001 | B2 | 8/2014 | Hoekstra et al. |
| 8,809,378 | B2 | 8/2014 | Hoekstra et al. |
| 8,883,797 | B2 | 11/2014 | Hoekstra et al. |
| 8,901,121 | B2 | 12/2014 | Hoekstra et al. |
| 8,940,735 | B2 | 1/2015 | Hoekstra et al. |
| 9,220,265 | B2 | 12/2015 | Hoekstra et al. |
| 9,221,791 | B2 | 12/2015 | Hoekstra et al. |
| 9,309,273 | B2 | 4/2016 | Hoekstra et al. |
| 9,414,596 | B2 | 8/2016 | Hoekstra et al. |
| 9,447,073 | B2 * | 9/2016 | Hoekstra ............ C07D 401/14 |
| 9,556,143 | B2 | 1/2017 | Hoekstra et al. |
| 9,663,488 | B2 | 5/2017 | Hoekstra et al. |
| 9,688,671 | B2 | 6/2017 | Hoekstra et al. |
| 2009/0318436 | A1 | 12/2009 | Albrecht et al. |
| 2011/0306644 | A1 | 12/2011 | Hoekstra et al. |
| 2012/0329788 | A1 | 12/2012 | Hoekstra et al. |
| 2012/0329802 | A1 | 12/2012 | Hoekstra et al. |
| 2013/0005719 | A1 | 1/2013 | Hoekstra et al. |
| 2013/0005729 | A1 | 1/2013 | Hoekstra et al. |
| 2013/0005752 | A1 | 1/2013 | Hoekstra et al. |
| 2013/0005776 | A1 | 1/2013 | Hoekstra et al. |
| 2013/0012503 | A1 | 1/2013 | Hoekstra et al. |
| 2014/0288107 | A1 | 9/2014 | Hoekstra et al. |
| 2014/0350003 | A1 | 11/2014 | Hoekstra et al. |
| 2015/0004666 | A1 | 1/2015 | Hoekstra et al. |
| 2015/0024938 | A1 | 1/2015 | Hoekstra et al. |
| 2015/0099750 | A1 | 4/2015 | Hoekstra et al. |
| 2016/0214959 | A1 | 7/2016 | Hoekstra et al. |
| 2017/0081285 | A1 | 3/2017 | Hoekstra et al. |
| 2017/0081309 | A1 | 3/2017 | Hoekstra et al. |
| 2017/0081310 | A1 | 3/2017 | Hoekstra et al. |
| 2017/0088539 | A1 | 3/2017 | Hoekstra et al. |
| 2017/0088540 | A1 | 3/2017 | Hoekstra et al. |
| 2017/0096410 | A1 | 4/2017 | Hoekstra et al. |
| 2017/0121307 | A1 | 5/2017 | Hoekstra et al. |
| 2017/0144990 | A1 | 5/2017 | Hokestra et al. |
| 2017/0144991 | A1 | 5/2017 | Hoekstra et al. |

(Continued)

FOREIGN PATENT DOCUMENTS

| CN | 1126722 A | 7/1996 |
| CN | 1334811 A | 2/2002 |
| JP | 2000-344744 A | 12/2000 |

(Continued)

OTHER PUBLICATIONS

International Search Report and Written Opinion dated Jun. 25, 2015 for Application No. PCT/US2015/021436.
International Search Report and Written Opinion dated Jun. 29, 2015 for Application No. PCT/US2015/021445.
International Search Report and Written Opinion dated Jun. 26, 2015 for Application No. PCT/US2015/021519.
International Search Report and Written Opinion dated Jun. 29, 2015 for Application No. PCT/US2015/021527.
International Search Report and Written Opinion dated Jul. 14, 2015 for Application No. PCT/US2015/021464.
International Search Report and Written Opinion dated Jul. 14, 2015 for Application No. PCT/US2015/021476.
International Search Report and Written Opinion dated Jul. 10, 2015 for Application No. PCT/US2015/021484.
International Search Report and Written Opinion dated Jun. 24, 2015 for Application No. PCT/US2015/021491.
International Search Report and Written Opinion dated Jun. 26, 2015 for Application No. PCT/US2015/021504.

(Continued)

*Primary Examiner* — Patricia L Morris
(74) *Attorney, Agent, or Firm* — Wolf, Greenfield, & Sacks, P.C.

(57) ABSTRACT

Provided herein are 2-(2,4-difluorophenyl)-1,1-difluoro-1-(5-substituted-pyridin-2-yl)-3-(1H-tetrazol-1-yl)propan-2-ols and processes for their preparation.

14 Claims, No Drawings

(56) References Cited

U.S. PATENT DOCUMENTS

2017/0158667 A1      6/2017   Hoekstra et al.

FOREIGN PATENT DOCUMENTS

| | | |
|---|---|---|
| WO | WO 00/37459 A1 | 6/2000 |
| WO | WO 2014-193974 A1 | 12/2004 |
| WO | WO 2009/020323 A2 | 2/2009 |
| WO | WO 2010/146113 A1 | 12/2010 |
| WO | WO 2010/147302 A2 | 12/2010 |
| WO | WO 2011/133875 A2 | 10/2011 |
| WO | WO 2012/177603 A2 | 12/2012 |
| WO | WO 2012/177608 A1 | 12/2012 |
| WO | WO 2012/177635 A1 | 12/2012 |
| WO | WO 2012/177725 A1 | 12/2012 |
| WO | WO 2012/177728 A1 | 12/2012 |
| WO | WO 2013/109998 A1 | 7/2013 |
| WO | WO 2013/110002 A1 | 7/2013 |
| WO | WO 2014/165861 A1 | 10/2014 |
| WO | WO 2015/143154 A1 | 9/2015 |
| WO | WO 2015/143162 A1 | 9/2015 |
| WO | WO 2015/143184 A1 | 9/2015 |
| WO | WO 2015/143192 A1 | 9/2015 |
| WO | WO 2016/187201 A2 | 11/2016 |
| WO | WO 2017/049080 A1 | 3/2017 |
| WO | WO 2017/049096 A1 | 3/2017 |
| WO | WO 2017/049196 A1 | 3/2017 |
| WO | WO 2017/087592 A1 | 5/2017 |
| WO | WO 2017/087597 A1 | 5/2017 |
| WO | WO 2017/087619 A1 | 5/2017 |
| WO | WO 2017/087643 A1 | 5/2017 |
| WO | WO 2017/117393 A1 | 7/2017 |

OTHER PUBLICATIONS

International Search Report and Written Opinion dated Jun. 24, 2015 for Application No. PCT/US2015/021511.
Partial Supplementary European Search Report and Search Opinion dated Jul. 13, 2017 for EP Application No. 15765715.6.
Partial Supplementary European Search Report and Search Opinion dated Aug. 3, 2017 for EP Application No. 15764600.1.
Extended European Search Report and Search Opinion dated Aug. 1, 2017 for EP Application No. 15764570.6.
Partial Supplementary European Search Report and Search Opinion dated Jul. 19, 2017 for EP Application No. 15764259.6.
Extended European Search Report and Search Opinion dated Jul. 3, 2017 for EP Application No. 15764654.8.
Extended European Search Report and Search Opinion dated Aug. 1, 2017 for EP Application No. 15764368.5.
Extended European Search Report and Search Opinion dated Jul. 21, 2017 for EP Application No. 15764743.9.
Extended European Search Report and Search Opinion dated Jul. 21, 2017 for EP Application No. 15764771.0.
Extended European Search Report and Search Opinion dated Jul. 13, 2017 for EP Application No. 15765307.2.
International Search Report and Written Opinion dated Feb. 3, 2017 for Application No. PCT/US2016/032877.
Biji, New Methodology for the Synthesis of $\alpha,\alpha$-difluoroketones. Syn. Comm. 2008; 38(12):1940-5. http://dx.doi.org/10.1080/00397910801997637.
Eto et al., New antifungal 1,2,4-triazoles with difluoro(heteroaryl)methyl moiety. Chem Pharm Bull (Tokyo). Jul. 2000;48(7):982-90.
Kolb et al., Catalytic Asymmetric Dihydroxylation. Chemical Reviews 1994;94(8):2483-2547. doi: 10.1021/cr00032a009.
Shimizu et al., Efficient method for preparation of N-methoxy-N-methyl amides by reaction of lactones or esters with Me2AlCl MeONHMe.HCl. Tetrahedron Letters. Apr. 1997;38(15):2685-8. https://doi.org/10.1016/S0040-4039(97)00429-2.
Uemura et al., Enantioselective Cyanosilylation of Ketones with Amino Acid/BINAP/Ruthenium(II)-Lithium Phenoxide Catalyst System. Advanced Synthesis & Catalysis. Jul. 2012;354(10):2023-30. doi: 10.1002/adsc.201200027.
Clemencon et al., Tandem Multicomponent/Click Reactions: Synthesis of Functionalized Oxazoles and Tetrazoles from Acyl Cyanides. Tetrahedron. 2007;63:8665-9.
Demko et al., A Click Chemistry Approach to Tetrazoles by Huisgen 1,3-Dipolar Cycloaddition: Synthesis of 5-Sulfonyl Tetrazoles from Azides and Sulfonyl Cyanides. Angew. Chem. Int. Ed. Dec. 2002; 41(12):2110-3.
Otsuki et al., Chemical tagging of a drug target using 5-sulfonyl tetrazole. Bioorg Med Chem Lett. Mar. 15, 2013;23(6):1608-11. doi:10.1016/j.bmcl.2013.01.092. Epub Jan. 30, 2013.

\* cited by examiner

2-(2,4-DIFLUOROPHENYL)-1,1-DIFLUORO-1-(5-SUBSTITUTED-PYRIDIN-2-YL)-3-(1H-TETRAZOL-1-YL)PROPAN-2-OLS AND PROCESSES FOR THEIR PREPARATION

CROSS REFERENCE TO RELATED APPLICATIONS

This application is the U.S. National Stage, pursuant to 35 U.S.C. § 371, of International Application No. PCT/US2015/021519, filed Mar. 19, 2015, which claims the benefit of U.S. Provisional Patent Application Ser. No. 61/955,661 filed Mar. 19, 2014, the entire disclosures of which are incorporated by reference herein.

FIELD

Provided herein are 2-(2,4-difluorophenyl)-1,1-difluoro-1-(5-substituted-pyridin-2-yl)-3-(1H-tetrazol-1-yl)propan-2-ols and processes for their preparation.

BACKGROUND

U.S. patent application Ser. Nos. 13/527,387, 13/527,426 and 13/528,283 describe inter alia certain metalloenzyme inhibitor compounds and their use as fungicides. The disclosure of each application is expressly incorporated by reference herein. Each of these patents describes the various routes to generate metalloenzyme inhibiting fungicides. It may be advantageous to provide more direct and efficient methods for the preparation of metalloenzyme inhibiting fungicides and related compounds, e.g., by the use of reagents and/or chemical intermediates which provide improved time and cost efficiency.

SUMMARY OF THE DISCLOSURE

Provided herein are 2-(2,4-difluorophenyl)-1,1-difluoro-1-(5-substituted-pyridin-2-yl)-3-(1H-tetrazol-1-yl)propan-2-ols and processes for their preparation. In one embodiment, provided herein is a process for the preparation of a compound of the Formula IV:

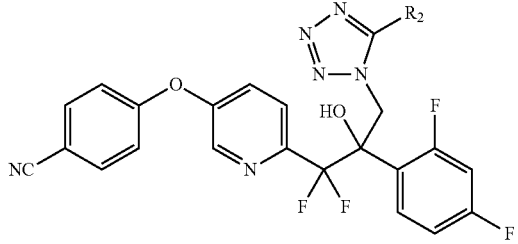
(IV)

wherein $R_2$ is selected from —$CO_2Et$, —C(O)Me, —C(O)Ph, or —$SO_2$(4-MePh),
which comprises contacting III with $R_2$—CN.

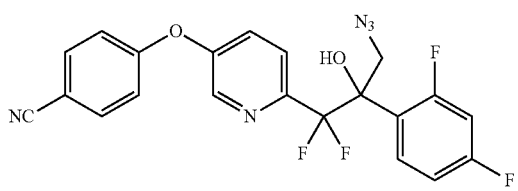
(III)

In another embodiment, III may be prepared by contacting II with sodium azide and a solvent.

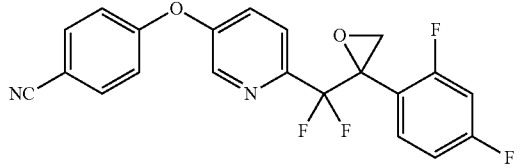
(II)

In another embodiment, II may be prepared by contacting I with trimethylsulfoxonium iodide and a base.

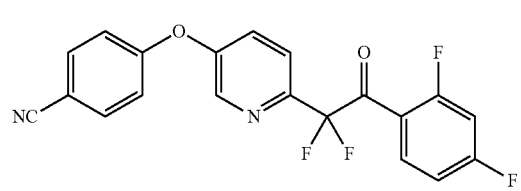
(I)

In another embodiment, VI may be prepared by contacting compounds of Formula IV wherein $R_2$ is —$CO_2Et$, with sodium hydroxide and contacting a mixture of IV and sodium hydroxide with hydrochloric acid.

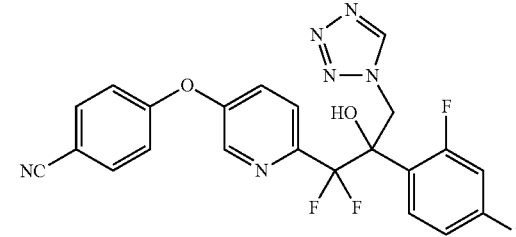
(VI)

In another embodiment, VI may be prepared by contacting compounds of Formula IV wherein $R_2$ is one of —C(O)Me and —C(O)Ph, with a base and a solvent.

In another embodiment, VI may be prepared by contacting compounds of Formula IV wherein $R_2$ is —$SO_2$(4-MePh), with Zn and an acid.

The term "cyano" refers to a —C≡N substituent.
The term "hydroxyl" refers to an —OH substituent.
The term "amino" refers to a —$NH_2$ substituent.
The term "alkylamino" refers to a —N(H)—R substituent.
The term "dialkylamino" refers to a —$NR_2$ substituent.
The term "halogen" or "halo" refers to one or more halogen atoms, defined as F, Cl, Br, and I.
The term "nitro" refers to a —$NO_2$ substituent.

The term "Lewis acid" refers to any substance that is an electron pair acceptor.

The term "organometallic" refers to an organic compound containing a metal, especially a compound in which a metal atom is bonded directly to a carbon atom.

Throughout the disclosure, references to the compounds of Formula V, IV, III, and II are read as also including optical isomers and salts. Specifically, when compounds of Formula V, IV, III, and II contain a branched chain alkyl group, it is understood that such compounds include optical isomers and racemates thereof. Exemplary salts may include: hydrochloride, hydrobromide, hydroiodide, and the like. Additionally, the compounds of Formula V, IV, III, and II may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

DETAILED DESCRIPTION 2-(2,4-Difluorophenyl)-1,1-difluoro-1-(5-substituted-pyridin-2-yl)-3-(1H-tetrazol-1-yl)propan-2-ols provided herein may be prepared from 4-((6-(2-(2,4-difluorophenyl)-1,1-difluoro-2-oxoethyl)pyridin-3-yl)oxy)benzonitrile as shown in Examples 1-7.

EXAMPLE 1

Preparation of 4-((6-((2-(2,4-difluorophenyl)oxiran-2-yl)difluoromethyl)pyridin-3-yl)oxy)benzonitrile

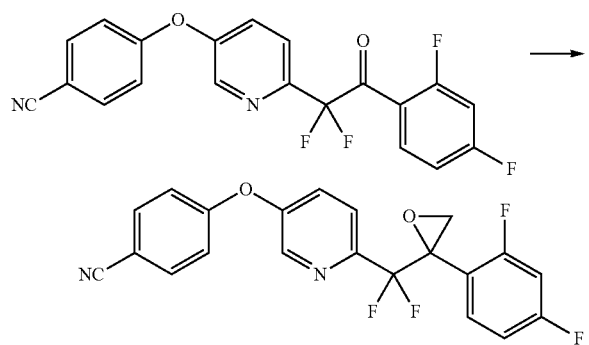

To a magnetically stirred solution of trimethylsulfoxonium iodide (2.67 g, 12.11 mmol) in dry THF/DMSO (1:1, 39 mL each) was added sodium hydride (0.485 g, 12.11 mmol) under a N₂ atmosphere. The reaction mixture was stirred at room temperature (rt) for 1 h, then cooled to 0° C. 4-((6-(2-(2,4-Difluorophenyl)-1,1-difluoro-2-oxoethyl)pyridin-3-yl)oxy)benzonitrile (4.00 g, 9.32 mmol) in THF (39 mL) was added slowly to maintain the temperature below 5° C. (internal temperature probe). The reaction was maintained at 0° C. for 30 min (TLC indicated complete conversion to product), and saturated sodium bicarbonate was added to quench the reaction. Brine was added, and the mixture was extracted with Et₂O. The combined organic phases were diluted with hexanes and washed with brine (2×) and water (1×), dried (MgSO₄) and concentrated to give the title compound as an amber oil (3.980 g, 96%): $^1$H NMR (300 MHz, CDCl₃) δ 8.46 (d, J=2.7 Hz, 1H), 7.73-7.62 (m, 2H), 7.52 (dd, J=8.6, 0.6 Hz, 1H), 7.48-7.35 (m, 2H), 7.13-7.02 (m, 2H), 6.92-6.80 (m, 1H), 6.75 (ddd, J=10.0, 8.9, 2.5 Hz, 1H), 3.46 (d, J=5.1 Hz, 1H), 3.03-2.96 (m, 1H); ESIMS m/z 401 ([M+H]⁺).

EXAMPLE 2

Preparation of 4-((6-(3-azido-2-(2,4-difluorophenyl)-1,1-difluoro-2-hydroxypropyl)pyridin-3-yl)oxy)benzonitrile

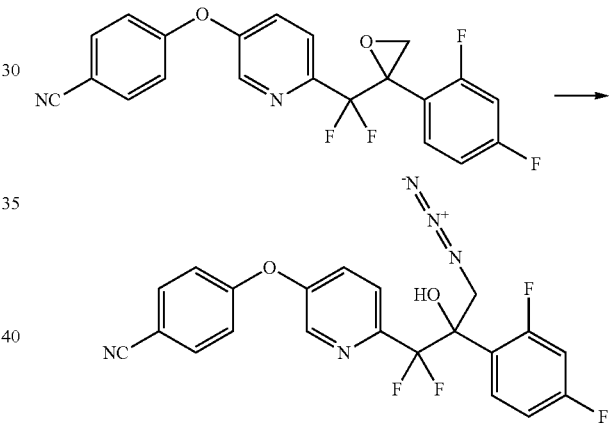

Method A: A solution of 4-((6-((2-(2,4-difluorophenyl)oxiran-2-yl)difluoromethyl)pyridin-3-yl)oxy)benzonitrile (3.5 g, 8.74 mmol) and sodium azide (1.705 g, 26.2 mmol) in DMF (43.7 mL) was heated at 50° C. for 17 hours. The reaction was poured into sat. aq. NaHCO₃, and the mixture was extracted with Et₂O (3×). The combined organic phases were washed with brine, dried (MgSO₄) and concentrated to give the title compound as a brown oil (3.353 g, 69%): $^1$H NMR (300 MHz, CDCl₃) δ 8.43 (m, 1H), 7.67 (m, 3H), 7.57 (d, J=8.7 Hz, 1H), 7.43 (dd, J=8.7, 2.7 Hz, 1H), 7.09 (m, 2H), 6.82 (m, 2H), 6.20 (s, 1H), 4.11 (m, 1H), 3.94 (dd, J=12.9, 2.3 Hz, 1H); ESIMS m/z 444 ([M+H]⁺).

Method B: A solution of 4-((6-((2-(2,4-difluorophenyl)oxiran-2-yl)difluoromethyl)pyridin-3-yl)oxy)benzonitrile (0.480 g, 1.199 mmol), sodium azide (0.234 g, 3.60 mmol) and ammonium chloride (0.192 g, 3.60 mmol) in MeOH (6.00 mL) was heated at 50° C. for 17 hours. The reaction was poured into sat. aq. NaHCO₃ and the mixture was extracted with Et₂O (3×). The combined organic phases were dried (MgSO₄) and concentrated to give the title compounds as a yellow oil (410 mg, 62%).

EXAMPLE 3

Preparation of ethyl 1-(3-(5-(4-cyanophenoxy)pyridin-2-yl)-2-(2,4-difluorophenyl)-3,3-difluoro-2-hydroxypropyl)-1H-tetrazole-5-carboxylate

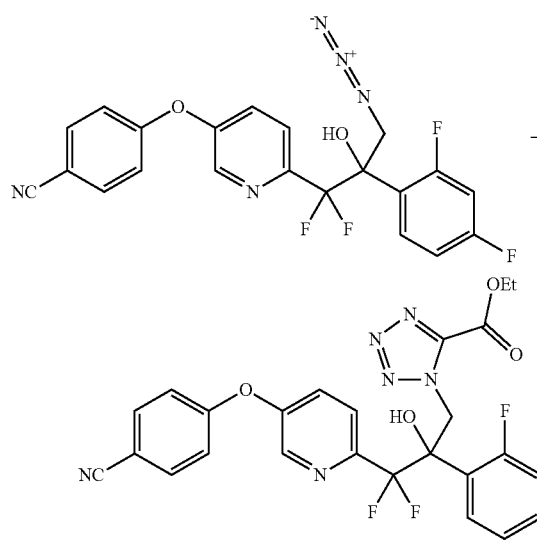

A mixture of 4-((6-(3-azido-2-(2,4-difluorophenyl)-1,1-difluoro-2-hydroxypropyl)pyridin-3-yl)oxy)benzonitrile (0.500 g, 0.902 mmol) and ethyl carbonocyanidate (0.134 mL, 1.353 mmol) was heated neat at 120° C. in a screw cap vial for 16 h. LCMS indicated complete conversion to the desired product. $^1$H NMR analysis of the crude indicated 80% conversion to product. The reaction mixture was diluted with DCM and purified by silica gel chromatography (0-100% EtOAc/hexanes) to give the title compound as a yellow oil (266 mg, 54%): $^1$H NMR (300 MHz, CDCl$_3$) δ 8.23 (d, J=2.7 Hz, 1H), 7.71 (m, 3H), 7.44 (m, 2H), 7.15 (m, 2H), 6.80 (m, 3H), 5.69 (d, J=14.2 Hz, 1H), 5.57 (d, J=14.4 Hz, 1H), 4.51 (q, J=7.1 Hz, 2H), 1.43 (t, J=7.2 Hz, 3H); IR (thin film) 2228, 1740 cm$^{-1}$; ESIMS m/z 444 ([M+H]$^+$).

EXAMPLE 4

Preparation of 4-((6-(3-(5-acetyl-1H-tetrazol-1-yl)-2-(2,4-difluorophenyl)-1,1-difluoro-2-hydroxypropyl)pyridin-3-yl)oxy)benzonitrile

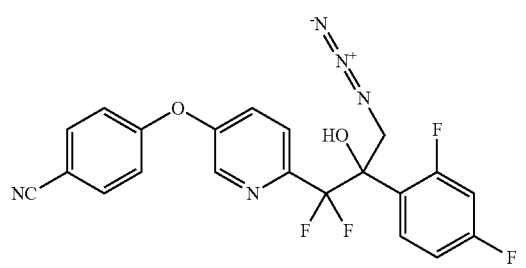

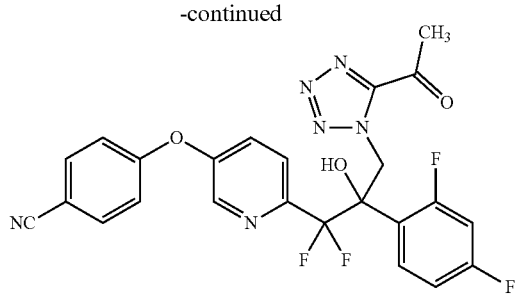

A mixture of 4-((6-(3-azido-2-(2,4-difluorophenyl)-1,1-difluoro-2-hydroxypropyl)pyridin-3-yl)oxy)benzonitrile (0.500 g, 0.902 mmol) and acetyl cyanide (0.096 mL, 1.353 mmol) was heated neat at 120° C. in a screw cap vial for 16 h. $^1$H NMR of the crude indicated 44% conversion to product. The reaction mixture was diluted with DCM and chromatographed (silica gel, 0-100% EtOAc/hexanes) to give the title compound as a yellow oil (104 mg, 23%): $^1$H NMR (300 MHz, CDCl$_3$) δ 8.35 (d, J=2.7 Hz, 1H), 7.70 (m, 3H), 7.48 (dd, J=8.7, 2.7 Hz, 1H), 7.36 (td, J=8.9, 6.5 Hz, 1H), 7.14 (m, 2H), 6.84 (m, 1H), 6.73 (m, 1H), 6.54 (s, 1H), 5.63 (d, J=14.0 Hz, 1H), 5.56 (d, J=14.9 Hz, 1H), 2.81 (s, 3H); IR (thin film) 2229, 1714 cm$^{-1}$; ESIMS m/z 513 ([M+H]$^+$).

EXAMPLE 5

Preparation of 4-((6-(3-(5-benzoyl-1H-tetrazol-1-yl)-2-(2,4-difluorophenyl)-1,1-difluoro-2-hydroxypropyl)pyridin-3-yl)oxy)benzonitrile

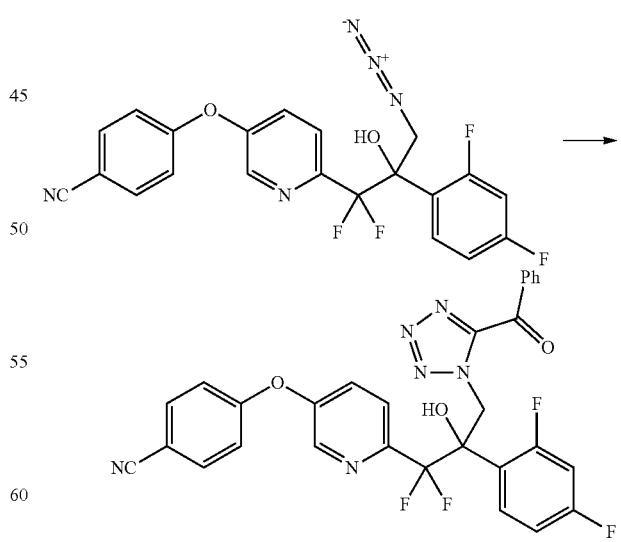

A mixture of 4-((6-(3-azido-2-(2,4-difluorophenyl)-1,1-difluoro-2-hydroxypropyl)pyridin-3-yl)oxy)benzonitrile (0.200 g, 0.361 mmol) and benzoyl cyanide (0.064 mL, 0.541 mmol) was heated neat at 120° C. in a screw cap vial for 16 h. ¹H NMR of the crude indicated 47% conversion to product. The reaction mixture was diluted with DCM and purified by silica gel chromatography (0-50% EtOAc/hexanes) to give the title compound as a yellow oil (73 mg, 32%): ¹H NMR (400 MHz, CDCl₃) δ 8.27 (d, J=2.7 Hz, 1H), 8.20 (dt, J=8.5, 1.5 Hz, 2H), 7.72 (m, 3H), 7.66 (app d, J=8.6 Hz, 1H), 7.56 (m, 2H), 7.46 (dd, J =8.6, 2.7 Hz, 1H), 7.31 (td, J=8.9, 6.5 Hz, 1H), 7.13 (m, 2H), 6.81 (ddd, J=12.0, 8.5, 2.6 Hz, 1H), 6.71 (m, 2H), 5.71 (d, J=14.2 Hz, 1H), 5.60 (dd, J=14.3, 1.0 Hz, 1H); IR (thin film) 2229, 1670 cm⁻¹; ESIMS m/z 575 ([M+H]⁺).

EXAMPLE 6

Preparation of 4-((6-(2-(2,4-difluorophenyl)-1,1-difluoro-2-hydroxy-3-(5-tosyl-1H-tetrazol-1-yl)propyl)pyridin-3-yl)oxy)benzonitrile

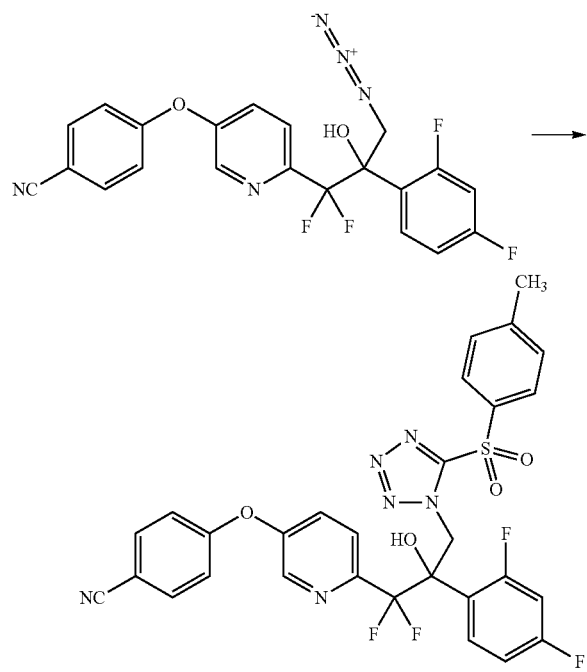

A mixture of 4-((6-(3-azido-2-(2,4-difluorophenyl)-1,1-difluoro-2-hydroxypropyl)pyridin-3-yl)oxy)benzonitrile (1.700 g, 3.07 mmol) and 4-methylbenzenesulfonyl cyanide (0.834 g, 4.60 mmol) was heated neat at 100° C. in a vial for 16 h. The reaction was cooled to room temperature, diluted with DCM and purified by silica gel chromatography (0-50% EtOAc/hexanes) to give the title compound as a faint yellow foam (1.109 g, 57%): ¹H NMR (300 MHz, CDCl₃) δ 8.37 (d, J=2.7 Hz, 1H), 7.98 (d, J=8.4 Hz, 2H), 7.73 (d, J=8.6 Hz, 1H), 7.68 (m, 2H), 7.51 (m, 2H), 7.42 (d, J=8.5 Hz, 2H), 7.13 (m, 2H), 6.83 (m, 2H), 6.67 (s, 1H), 5.70 (d, J=13.7 Hz, 1H), 5.58 (d, J=14.2 Hz, 1H), 2.48 (s, 3H); IR (thin film) 3107, 2229, 1158 cm⁻¹; ESIMS m/z 626 ([M+H]⁺).

EXAMPLE 7

Preparation of 4-((6-(2-(2,4-difluorophenyl)-1,1-difluoro-2-hydroxy-3-(1H-tetrazol-1-yl)propyl)pyridin-3-yl)oxy)benzonitrile

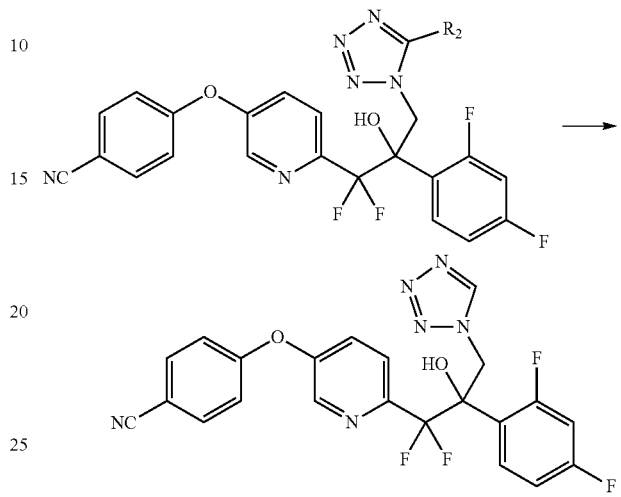

R₂=—CO₂Et, —COMe, —COPh, —SO₂(4-MePh)

Method A: By saponification/decarboxylation of ethyl ester and extraction. To a solution of ethyl 1-(3-(5-(4-cyanophenoxy)pyridin-2-yl)-2-(2,4-difluorophenyl)-3,3-difluoro-2-hydroxypropyl)-1H-tetrazole-5-carboxylate (0.097 g, 0.179 mmol) in EtOH (0.203 mL) and water (2.032 mL) at room temperature was added 2N sodium hydroxide (0.447 mL, 0.894 mmol). The reaction was stirred at room temperature for 30 min. The reaction was then acidified with 1N HCl, resulting in an off-white precipitate forming. The mixture was extracted with EtOAc, and the combined organic phases were dried (MgSO₄) and concentrated to the give the title compound as a faint yellow oil (83 mg, 99%): ¹H NMR (300 MHz, CDCl₃) δ 8.74 (s, 1H), 8.26 (d, J=2.7 Hz, 1H), 7.71 (m, 2H), 7.62 (d, J=8.7 Hz, 1H), 7.43 (m, 2H), 7.19 (s, 1H), 7.12 (m, 2H), 6.76 (m, 2H), 5.44 (d, J=14.4 Hz, 1H), 5.23 (dd, J=14.4, 1.5 Hz, 1H); ESIMS m/z 469 ([M−H]⁻).

Method B: By saponification/decarboxylation of ethyl ester and filtration. To a solution of ethyl 1-(3-(5-(4-cyanophenoxy)pyridin-2-yl)-2-(2,4-difluorophenyl)-3,3-difluoro-2-hydroxypropyl)-1H-tetrazole-5-carboxylate (0.142 g, 0.262 mmol) in EtOH (0.238 mL) and water (2.380 mL) at room temperature was added 2N sodium hydroxide (0.654 mL, 1.309 mmol). The reaction was stirred at room temperature for 30 min. The reaction was acidified with 1N HCl, resulting in an off-white precipitate forming, which was isolated by filtration, washing with water. The solid was dried under vacuum for 2 h to give the title compound as a white crystalline solid (106 mg, 86%).

Method C: By deacylation with piperidine. To a solution of 4-((6-(3-(5-acetyl-1H-tetrazol-1-yl)-2-(2,4-difluorophenyl)-1,1-difluoro-2-hydroxypropyl)pyridin-3-yl)oxy)benzonitrile (0.045 g, 0.088 mmol) in EtOH (0.220 mL) at room temperature was added piperidine (8.69 μl, 0.088 mmol). The reaction was stirred at room temperature overnight. Product had begun to form after 18 h, but some starting material remained. The reaction was heated at 40° C. for 24 h. LCMS indicated complete consumption of starting material. 1N HCl was added, and the mixture was extracted with DCM. The combined organic phases were dried (MgSO$_4$) and concentrated to give the title compound as a faint yellow oil (37 mg, 67%).

Method D: By deacylation with sodium hydroxide. To a solution of 4-((6-(3-(5-acetyl-1H-tetrazol-1-yl)-2-(2,4-difluorophenyl)-1,1-difluoro-2-hydroxypropyl)pyridin-3-yl)oxy)benzonitrile (0.045 g, 0.088 mmol) in EtOH (0.439 mL) at room temperature was added 10% aqueous sodium hydroxide (0.070 mL, 0.176 mmol). The reaction was stirred at room temperature for 1 h, after which TLC analysis indicated complete consumption of starting material. 1N HCl was added, and an off-white precipitate formed. The mixture was extracted with DCM, and the combined organic phases were dried (MgSO$_4$) and concentrated to give the title compound as a faint yellow oil (33 mg, 76%).

Method E: By debenzoylation with sodium hydroxide. To a solution of 4-((6-(3-(5-benzoyl-1H-tetrazol-1-yl)-2-(2,4-difluorophenyl)-1,1-difluoro-2-hydroxypropyl)pyridin-3-yl)oxy)benzonitrile (0.058 g, 0.091 mmol) in EtOH (0.454 mL) at room temperature was added 10% sodium hydroxide (0.073 mL, 0.182 mmol). The reaction was stirred at room temperature for 30 min, after which TLC analysis indicated complete consumption of starting material. 1N HCl was added, and an off-white precipitate formed. The mixture was extracted with DCM, and the combined organic phases were dried (MgSO$_4$) and concentrated to give the title compound as a faint yellow oil (39 mg, 91%).

Method F: By desulfonylation. To a solution of 4-((6-(2-(2,4-difluorophenyl)-1,1-difluoro-2-hydroxy-3-(5-tosyl-1H-tetrazol-1-yl)propyl)pyridin-3-yl)oxy)benzonitrile (0.100 g, 0.160 mmol) in acetic acid (3.20 mL) was added zinc powder (0.105 g, 1.601 mmol). The reaction was heated at 60° C. for 5 h, after which LCMS indicated 53% conversion to product. Additional Zn was added, and the reaction was heated at 90° C. for 3 h. The reaction was filtered through a plug of celite washing with acetic acid. The mixture was concentrated to 1 mL, and water was added. The mixture was carefully neutralized with saturated aqueous NaHCO$_3$ and the mixture was extracted with DCM. The combined organic phases were dried (MgSO$_4$) and concentrated. The residue was purified by silica gel chromatography (0-50% EtOAc/hexanes) to give the title compound as a colorless oil (33 mg, 44%).

BIOLOGICAL EXAMPLES

Example A

Evaluation of Fungicidal Activity: Leaf Blotch of Wheat (*Mycosphaerella Graminicola*; Anamorph: *Septoria Tritici*; Bayer Code SEPTTR)

Technical grades of materials shown in Table 1 below were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1st leaves of untreated plants, infection levels were assessed on a scale of 0 to 100 percent disease severity. Percent disease control was calculated using the ratio of disease severity on treated plants relative to untreated plants. The results are shown below in Table 1.

Example B

Evaluation of Fungicidal Activity: Wheat Brown Rust (*Puccinia Triticina*; Synonym: *Puccinia Recondita* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A. The results are shown below in Table 1.

In each case of Table 1, the *Septoria* and *Puccinia* rating scale is as follows:

| % Disease Control at 50 ppm | Rating |
|---|---|
| 80-100 | A |
| 60-79 | B |
| 40-59 | C |
| <40 | D |
| Not tested | E |

TABLE 1

Biological Data for Compounds of Formula (IV)

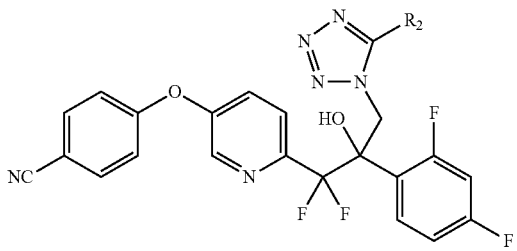

(IV)

| R$_2$ | SEPTTR* | | PUCCRT* | |
| | 1DP* | 3DC* | 1DP* | 1DC* |
|---|---|---|---|---|
| —CO2Et | A | A | A | A |
| —C(O)Me | A | A | A | A |
| —C(O)Ph | C | C | A | D |
| —SO2(4-MePh) | C | D | D | A |

*SEPTTR—Wheat Leaf Blotch (*Septoria tritici*)
*PUCCRT—Wheat Leaf Rust (*Puccinia recondita tritici*)
*1DP—1 Day Protectant
*3DC—3 Day Curative
*1DC—1 Day Curative

What is claimed is:

1. A method of making compounds of the Formula IV:

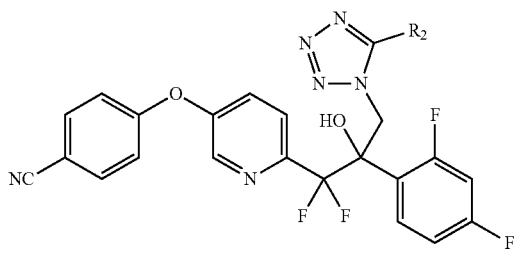

by contacting a compound of Formula III with R$_2$—CN,

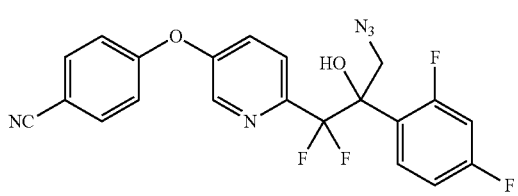

wherein R$_2$ is selected from —CO$_2$Et, —C(O)Me, —C(O)Ph, and —SO$_2$(4-MePh).

2. The method of claim 1, wherein the step of contacting compounds of Formula III with R$_2$—CN is carried out between 90° C. and 130° C.

3. The method of claim 1, further comprising the step of contacting a compound of Formula II with sodium azide and a solvent

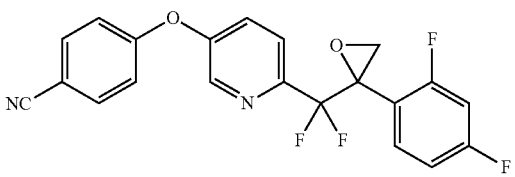

4. The method of claim 3, wherein the solvent is selected from dimethylformamide and methanol.

5. The method of claim 3, wherein the step of contacting the compound of Formula II with sodium azide and a solvent is carried out between 40° C. and 60° C.

6. The method of claim 3, further comprising the step of contacting the compound of Formula I with trimethylsulfoxonium iodide and a base

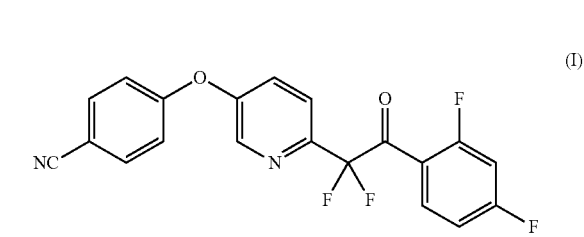 [SMILES: N#Cc1ccc(Oc2ccc(C(F)(F)C(=O)c3ccc(F)cc3F)nc2)cc1]

7. The method the claim 6, wherein the base is sodium hydride.

8. The method of claim 1, wherein R$_2$ is —CO$_2$Et, further comprising the steps of:

contacting a compound of Formula IV with sodium hydroxide forming a mixture; and contacting the mixture with hydrochloric acid.

9. The method of claim 1, wherein R$_2$ is one of —C(O)Me and —C(O)Ph, further comprising the step of:

contacting the compound of Formula IV with a base and a solvent.

10. The method of claim 9, wherein the solvent is ethanol.

11. The method of claim 9, wherein base is one of sodium hydroxide and piperidine.

12. The method of claim 9, wherein the step of contacting the compound of Formula IV with the base and the solvent is carried out between 60° C. and 90° C.

13. The method of claim 1, wherein R$_2$ is —SO$_2$(4-MePh), further comprising the step of:

contacting the compound of Formula IV with Zn and an acid.

14. The method of claim 13, wherein the acid is acetic acid.

* * * * *